US010722424B2

(12) United States Patent
Giraud et al.

(10) Patent No.: US 10,722,424 B2
(45) Date of Patent: Jul. 28, 2020

(54) MASSAGE DEVICE WITH MASSAGE HEAD PROVIDED WITH A PADDLE ROLLER AND A SMOOTH ROLLER

(71) Applicant: SEB S.A., Ecully (FR)

(72) Inventors: Camille Giraud, Lyons (FR); Franck Mandica, Francheville (FR); Monique Paget, Optevoz (FR)

(73) Assignee: SEB S.A. (FR)

( * ) Notice: Subject to any disclaimer, the term of this patent is extended or adjusted under 35 U.S.C. 154(b) by 1137 days.

(21) Appl. No.: 15/030,098

(22) PCT Filed: Oct. 15, 2014

(86) PCT No.: PCT/FR2014/052631
§ 371 (c)(1),
(2) Date: Apr. 18, 2016

(87) PCT Pub. No.: WO2015/055954
PCT Pub. Date: Apr. 23, 2015

(65) Prior Publication Data
US 2016/0262973 A1    Sep. 15, 2016

(30) Foreign Application Priority Data
Oct. 17, 2013  (FR) ..................................... 13 60119

(51) Int. Cl.
*A61H 15/02*    (2006.01)
*A61N 1/04*    (2006.01)
(Continued)

(52) U.S. Cl.
CPC ............. *A61H 15/02* (2013.01); *A61H 15/00* (2013.01); *A61H 15/0078* (2013.01);
(Continued)

(58) Field of Classification Search
CPC ................ A61H 7/005; A61H 23/0254; A61H 15/0085; A61H 15/02; A61H 2205/022;
(Continued)

(56) References Cited

U.S. PATENT DOCUMENTS

| 448,883 | A | * | 3/1891 | Kahn | ..................... A61H 15/00 601/122 |
| 1,872,832 | A | * | 8/1932 | Silverberg | ............. A61H 13/00 601/141 |

(Continued)

FOREIGN PATENT DOCUMENTS

| EP | 0666071 A1 | 8/1995 |
| EP | 0916330 A1 | 5/1999 |

(Continued)

OTHER PUBLICATIONS

English translation for FR2797183, Espacenet.com, translated on Mar. 14, 2020.*

*Primary Examiner* — Tu A Vo
(74) *Attorney, Agent, or Firm* — Lerner, David, Littenberg, Krumholz & Mentlik, LLP (57) ABSTRACT

Provided is a facial massage device including: —a massage head that includes: —two parallel massage rollers that are mobiles in rotation on themselves about two rotational axes parallel to each other and to the application surface (S), and set apart from each other, being separated by a working area (Z), a first roller including at least one paddle that extends radially projecting from the surface of the first roller, and the second roller having a smooth surface, —transmission assembly designed to rotate the rollers in the same direction, the first roller moving from outside the working area (Z) to inside the working area (Z), and the second roller moving from inside the working area to outside the working area, when viewed from outside the massage head, —and a drive housing that carries the massage head and that includes an
(Continued)

electric motor that actuates drive means designed to transmit the drive from the electric motor to the transmission means.

44 Claims, 4 Drawing Sheets

(51) Int. Cl.
| | | |
|---|---|---|
| *A61N 5/06* | (2006.01) | |
| *A61H 15/00* | (2006.01) | |
| *A61N 1/32* | (2006.01) | |

(52) U.S. Cl.
CPC .......... *A61H 15/0085* (2013.01); *A61N 1/04* (2013.01); *A61N 1/0428* (2013.01); *A61N 1/322* (2013.01); *A61N 5/06* (2013.01); *A45D 2200/057* (2013.01); *A61H 2015/0014* (2013.01); *A61H 2201/10* (2013.01); *A61H 2201/1207* (2013.01); *A61H 2201/1215* (2013.01); *A61H 2201/5025* (2013.01); *A61H 2205/022* (2013.01); *A61N 2005/0652* (2013.01)

(58) Field of Classification Search
CPC .... A61H 2201/1207; A61H 2201/5025; A61H 2201/1472; A61H 2201/0188; A61H 2201/1215; A61H 2015/0064; A61H 2201/1685; A61H 2201/1692; A61H 2201/10; A61H 15/00; A61H 2015/0007; A61H 2015/0014; A61H 2015/0021; A61H 2015/0028; A61H 2015/0035; A61H 2015/0042; A61H 2015/005; A61H 2015/0057; A61H 2015/0071; A61H 15/0078; A61H 15/0092; A61H 19/00; A61H 19/30; A61H 19/34; A61H 19/50; A61H 7/004; A61H 7/008; A61H 2007/009; A46B 15/0036; A46B 2200/102; A61N 5/0616; A61N 2005/0666; A61N 2005/0662; A61N 2005/0652; A61N 2005/0644; A61N 2005/0659; A61B 2017/00734; A61B 2017/00747

See application file for complete search history.

(56) References Cited

U.S. PATENT DOCUMENTS

| | | | | |
|---|---|---|---|---|
| 2,003,272 A * | 5/1935 | Betz | ................ | A61H 15/0085 601/133 |
| 2,095,634 A * | 10/1937 | Gibson | ............. | A61H 23/0254 601/111 |
| 2,183,726 A * | 12/1939 | Sommer | ................ | A61H 15/02 601/17 |
| 2,547,115 A * | 4/1951 | Folley | ................... | A61H 15/00 601/119 |
| 3,297,024 A * | 1/1967 | Robinson | ............... | A61H 7/005 601/7 |
| 3,626,934 A | 12/1971 | Andis | | |
| 3,878,837 A * | 4/1975 | Werding | ............ | A61H 15/0085 601/148 |
| 4,046,142 A * | 9/1977 | Whitney | ................ | A61H 7/005 601/108 |
| 4,412,535 A * | 11/1983 | Teren | ................. | A61H 15/0078 446/456 |
| 4,481,939 A * | 11/1984 | Mabuchi | ............ | A61H 15/0085 601/118 |
| 4,546,765 A * | 10/1985 | Adams | ................... | A61H 7/005 601/111 |
| 4,729,368 A * | 3/1988 | Guitay | ................... | A61H 7/008 601/123 |
| 4,858,600 A * | 8/1989 | Gross | ................. | A61H 15/0085 601/159 |
| 5,735,804 A * | 4/1998 | Chan | ..................... | A43B 7/146 36/141 |
| 5,891,064 A * | 4/1999 | Van Herk | ............. | A61H 7/008 601/122 |
| 5,935,088 A * | 8/1999 | Bosley | ................... | A61H 7/008 15/344 |
| 6,010,264 A * | 1/2000 | Scuderi | ............... | A45D 34/041 401/209 |
| 6,017,320 A * | 1/2000 | Bleeker | ................... | A61H 7/005 601/122 |
| 6,090,055 A * | 7/2000 | Frajdenrajch | ......... | A61H 7/008 15/344 |
| 6,517,499 B1 * | 2/2003 | Pereira | ................... | A61H 7/008 601/125 |
| 6,585,667 B1 * | 7/2003 | Muller | ................... | A61H 7/008 601/6 |
| 6,663,580 B1 * | 12/2003 | Adams | ................... | A61H 7/005 601/111 |
| 6,925,672 B1 * | 8/2005 | Bromley | ............ | A61H 15/0092 15/104.94 |
| 8,348,866 B2 * | 1/2013 | Tudico | ................... | A61H 7/005 601/7 |
| 9,066,844 B2 | 6/2015 | Thiebaut | | |
| 2003/0073937 A1 * | 4/2003 | Guitay | ................... | A61H 7/008 601/6 |
| 2003/0120185 A1 * | 6/2003 | Dirks | ................. | A61H 15/0085 601/15 |
| 2004/0208683 A1 * | 10/2004 | Shawan | ............... | A45D 34/041 401/6 |
| 2004/0260209 A1 | 12/2004 | Ella et al. | | |
| 2006/0259102 A1 * | 11/2006 | Slatkine | ............... | A61B 17/205 607/88 |
| 2007/0123807 A1 * | 5/2007 | Applebaum | ....... | A61H 15/0085 601/20 |
| 2007/0173749 A1 * | 7/2007 | Williams | ................. | A61H 7/00 601/123 |
| 2008/0014011 A1 * | 1/2008 | Rossen | ................ | A45D 34/041 401/195 |
| 2008/0154162 A1 * | 6/2008 | Thiebaut | ................ | A61H 7/003 601/125 |
| 2008/0183252 A1 * | 7/2008 | Khen | .................... | A61B 18/14 607/101 |
| 2010/0049177 A1 * | 2/2010 | Boone, III | .......... | A61H 9/0057 606/9 |
| 2010/0160840 A1 * | 6/2010 | Murphy | ................ | A61H 7/005 601/112 |
| 2012/0209151 A1 * | 8/2012 | Zhou | .................... | A61H 23/0245 601/2 |

FOREIGN PATENT DOCUMENTS

| | | | |
|---|---|---|---|
| EP | 1932500 A1 | 6/2008 | |
| FR | 2797183 A1 * | 2/2001 | ............ A61H 9/005 |
| JP | 2000210360 A | 8/2000 | |
| KR | 20090091414 A | 8/2009 | |
| WO | 2010094888 A1 | 8/2010 | |

* cited by examiner

MASSAGE DEVICE WITH MASSAGE HEAD PROVIDED WITH A PADDLE ROLLER AND A SMOOTH ROLLER

CROSS-REFERENCE TO RELATED APPLICATIONS

This application is the United States national phase of International Application No. PCT/FR2014/052631 filed Oct. 15, 2014, and claims priority to French Patent Application No. 1360119 filed Oct. 17, 2013, the disclosures of which are hereby incorporated in their entirety by reference.

FIELD OF THE INVENTION

This invention pertains to the field of skin treatment devices, particularly for the face. The device described in the invention is used, at a minimum, to tone skin by massaging it. The massage device described in the invention is intended for use by people who wish to look after their appearance by sculpting, firming and rejuvenating their skin, and the face in particular.

DESCRIPTION OF THE RELATED ART

Skin massage devices generally consist of a body, equipped with a power means, and a massage head that comprises massage components configured to be propelled by the power means, by a transmission mechanism. The prior art in this field includes patents and patent applications EP 0 666 071 A1 and U.S. Pat. No. 3,626,934.

In Document EP 0 666 071 A1, the massage device comprises two paddle-shaped components that turn in opposite directions to move said paddles toward one another to fold the skin. In one variation, this massage device comprises a flexible wire component that forms a loop, the two ends of which are spun in opposite directions, allowing the looped part to fold the skin.

In Document U.S. Pat. No. 3,626,934, a skin massage device is described with two fingers that reproduce an alternating tapping along one axial direction of each finger toward the skin. The system has fingers in the form of hammers with a large surface area, of which only one hammer in two comes into contact with the skin.

In Document U.S. Pat. No. 4,046,142, the facial massage device comprises a roller that is spun, and the roller is equipped with paddles.

In Document JP2000210360, the skin massage device comprises a roller with flexible teeth or paddles, in several variations of teeth or paddles, in order to produce a simultaneous and continuous beating and rubbing massage.

In Document EP1932500, the non-electric, manual massage device comprises a method of implementation with two rollers, one with a smooth surface that is fixed with respect to the casing, and another that can spin freely with respect to the casing, equipped with regular protruding ribs.

Such massage devices can therefore be used to perform a "stretching" or "pinching" type of massage. However, since this type of massage is not the only one capable of rejuvenating and/or firming facial skin, the need has arisen, in particular, for a device that can perform other types of massage or stimulation. Thus, the purpose of the invention is to provide a massage device that can perform a light pinching massage to imitate the "Jacquet pinching" type of massage performed by professional beauticians using the thumb and index finger in a delicate manner. The invention also aims to provide a massage device that performs a light massage so that it can be used in sensitive areas such as the neck or face, while being sized appropriately for these areas.

SUMMARY OF THE INVENTION

In order to meet these objectives, the first aspect of the invention pertains to a facial massage device comprising:

A massage head comprising:
  Two parallel massage rollers that are mobile in rotation on themselves about two rotational axes parallel to each other and to the application surface, set apart from each other, being separated by a working area, a first roller comprising at least one paddle that protrudes radially from the surface of the first roller, and the second roller having a smooth-type surface,
  A transmission means designed to spin the rollers in the same direction, the first roller moving from outside the working area to inside the working area, and the second roller moving from inside the working area to outside the working area, when viewed from outside the massage head,
And a drive housing that carries the massage head and that comprises an electric motor that actuates a drive means designed to transmit the movement of the electric motor to the transmission means.

The term "smooth-type surface" or "smooth surface" refers to a surface that does not have any paddles or pronounced protrusions with respect to the length of the diameter of the roller in question. Such a surface is a surface that is smooth enough to remain at least partially in contact with the skin at any moment while the roller is spinning on the skin; it is shaped such that the roller is in contact with the skin without pinching or pulling it. Such a surface can be an absolutely smooth surface or a surface with protrusions that are not very tall with respect to the diameter of the roller (less than one-third of the diameter, for example). Consequently, the slight protrusions from this smooth-type surface may create a textured surface, a fluted surface, or a slightly wavy surface, which makes it possible to more effectively catch the skin by contact, thereby preventing it from sliding over the skin. This is the type of smooth surface referred to in this application, in contrast to the outside surface of the other roller with one or more paddles.

The combination of a paddle roller with a smooth-surface roller makes it possible, on the one hand, to reproduce the Jacquet pinching action and, on the other hand, to pinch effectively without causing pain or harm, such as bruising, for example. Indeed, the device is surprisingly capable of reproducing the movement of the thumb along the wrinkle via the "back" roller, to "catch" the skin and guide the user without sliding over the skin. The pinch of the index finger is reproduced by a "front" roller with at least one paddle, which is motorized and spins at a different speed than the back roller.

In one characteristic of the first aspect of the invention, the transmission means is designed to spin the rollers simultaneously. The phrase "simultaneous spinning of the rollers" means that the motorized spinning occurs at the same time for the first and second rollers. Of course, this term in no way limits the relative spinning speed of the rollers.

In one characteristic of the first aspect of the invention, the transmission means is designed to ensure that the spinning speed of the first roller is greater than the spinning speed of the second roller. Thus, the second roller controls the speed at which the massage head moves forward over the skin, while the first roller produces the pinching.

In one variation of this characteristic, the transmission means is designed to ensure that the spinning speed of the first roller is between double and triple the spinning speed of the second roller, including the terminals, and preferably double.

In one characteristic of the first aspect of the invention, a plane tangent to the two rollers and situated toward the outside of the massage head, forms a non-zero, non-right angle with a longitudinal axis of the housing. Such a configuration makes it possible to achieve comfort of use by making it possible to hold the drive housing on a slight incline with respect to the surface of the skin where the massage is performed.

To attain these objectives, a second aspect of the invention pertains to a facial massage device comprising:

A massage head comprising:
Two parallel massage rollers that are mobile in rotation on themselves about two rotational axes parallel to each other and to the application surface, set apart from each other, being separated by a working area, a first roller comprising at least one paddle that protrudes radially from the surface of the first roller, and the second roller having a smooth-type surface,
And a drive housing that carries the massage head
A plane tangent to the two rollers and situated toward the outside of the massage head, forms a non-zero, non-right angle with a longitudinal axis of the housing.

The term "smooth-type surface" or "smooth surface" is the same as for the motorized facial massage device described above. This type of manual device, which does not have a system of motorizing the massage head, simplifies the device and its production and makes it more compact. This also makes it possible to provide a facial massage device at a lower cost. The inclined shape of the massage head with respect to the housing ensures comfort of use while making it possible to hold the drive housing at a slight incline with respect to the surface of the skin being massaged.

In one alternative of the second aspect of the invention, the massage head comprises a transmission means designed to spin the rollers in the same direction, the first roller moving from outside the working area to inside the working area, and the second roller moving from inside the working area to outside the working area, when viewed from outside the massage head, In this alternative, the drive housing comprises an electric motor that actuates the drive means designed to transmit the movement of the electric motor to the transmission means.

Advantageously, the transmission means comprises a gear box that is designed to spin the rollers simultaneously. The phrase "simultaneous spinning of the rollers" means that the motorized spinning occurs at the same time for the first and second rollers. Of course, this term in no way limits the relative spinning speed of the rollers.

Additionally, the transmission means comprises a gear box designed to ensure that the spinning speed of the first roller is faster than the spinning speed of the second roller. Thus, the second roller controls the speed at which the massage head moves forward over the skin, while the first roller produces the pinching.

In one variation of this motorization characteristic, the transmission means comprises a gear box designed to ensure that the spinning speed of the first roller is between double and triple the spinning speed of the second roller, including the terminals, and preferably double.

Certain other technical characteristics can be considered either for the first aspect or the second aspect of the invention, such as:

In another characteristic of the invention, the first roller comprises at least two paddles distributed regularly around its periphery.

In another characteristic of the invention, the first roller comprises at least one paddle that, in its crosswise straight cross-section, is straight in shape.

In another characteristic of the invention, the first roller comprises at least one paddle that, in its crosswise straight cross-section, is shaped like a figure-8.

In another characteristic of the invention, the first roller comprises at least one paddle that, in its crosswise straight cross-section, is elongated and slender in shape, the thickness of which tapers toward the end. In other words, this shape can take on the form commonly known as a comma, for example, the concavity of which is situated, when at rest, opposite the spinning direction of the first roller.

In another characteristic of the invention, the first roller comprises at least one paddle that, in its crosswise straight cross-section, has a free end that is thicker than the rest of the paddle.

In another characteristic of the invention, the first roller comprises at least one paddle that, in its crosswise straight cross-section, is shaped like an uppercase L, the base of which is at the free end of the paddle. The top end of the L is attached to the roller.

In one characteristic of the invention, the massage head of the massage device described in the invention comprises an application surface designed to come at least partially into contact with the skin. The one or more paddle(s) of the second roller protrude with respect to the pressure surface. The application surface may be arranged at least at the level of one roller and on each side of said roller. It can extend along and on each side of the two rollers and the working area. In a first method, the smooth-type surface can protrude slightly with respect to the pressure surface; in a second method, it can be at the same level as the application surface or, in other words, the smooth-type surface is flush with the application surface. The application surface balances the application of the two rollers on the skin by providing a static point of reference with respect to the massage head, or even with respect to the housing held by the user.

In one characteristic of the invention, the massage device described in the invention comprises a means of applying an electric current comprising at least one electrode, which is designed to be in contact with the skin and which is connected to an electric current and/or voltage generator unit. The use of such a means of applying an electric current makes it possible to apply a low current to the skin, particularly in such a way as to induce electrophoresis and/or iontophoresis phenomena, which promote the penetration of active principles applied to the skin before and/or during the massage.

In one variation of this characteristic, the application surface carries at least one electrode.

In another variation of this characteristic, a roller carries or forms at least one electrode.

In another characteristic of the invention, the massage device comprises a means of diffusing light. It is designed to emit light toward the face. The use of such a light diffusing means makes it possible to perform a phototherapy treatment and/or activate the active principles applied to the skin before and/or during the massage.

In one variation of this characteristic, the light diffusion means comprises at least one light source and at least one optical diffusion system comprising an output surface designed to be oriented toward the face.

In another variation of this characteristic, the application surface comprises a light output surface.

In another variation of this characteristic, the massage head comprises a light output surface situated facing the working area.

In one characteristic of the invention, the massage device comprises a means of applying a cosmetic product. The use of such a means of application makes it possible to deposit a cosmetic product on the skin before and/or during the massage.

In one variation of this characteristic, the means of applying the cosmetic product comprises at least one cap that comprises a swab soaked in the cosmetic product, which is designed to be removable from the massage head.

In another variation of this characteristic, the means of applying the cosmetic product comprises a reservoir of the cosmetic product and at least one dispensing nozzle connected to a system for withdrawing the cosmetic product from the reservoir. The withdrawing system can include, for example, an electrical pump or even a peristaltic pump activated by the drive means.

In another variation of this characteristic, the means of applying the cosmetic product comprises at least one dispensing nozzle situated in the massage head or on the application surface.

In one characteristic of the invention, the massage head is designed to be removable from the drive housing. The removable nature of the massage head makes it possible to use several interchangeable massage heads with the same housing.

In one variation of this characteristic, the massage head comprises an identification means and the drive housing comprises a means of recognizing the identification means connected to a control unit designed to control the operation of the massage device, depending on the massage head recognized. The use of such an identification system makes it possible to automatically adjust the operation of the massage device, such that the user does not have to be concerned with it.

Of course, the different characteristics, variations and implementation methods of the invention can be combined with one another in various combinations to the extent that they are not incompatible or mutually-exclusive.

BRIEF DESCRIPTION OF THE DRAWINGS

Moreover, various other characteristics of the invention will become apparent in the included description, provided in reference to the drawings, which illustrate non-limiting methods of implementing a massage device described in the invention.

DETAILED DESCRIPTION OF THE INVENTION

It should be noted that in these drawings, the structural and/or functional components common to the different variations may bear the same reference numbers.

Figure 1:
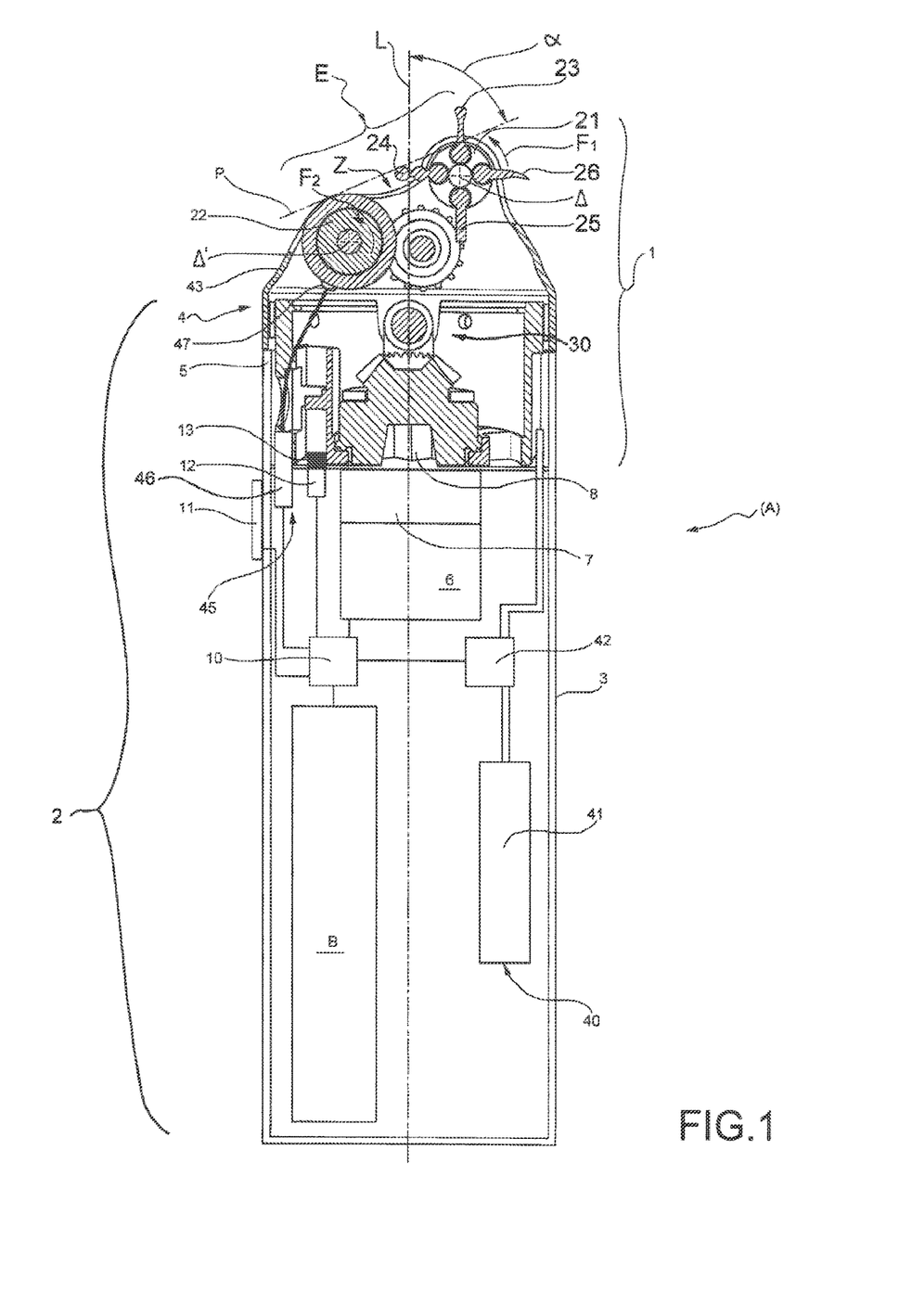
FIG. 1 is a cross-section illustration of a massage device described in the invention.

A massage device described in the invention, as illustrated in FIG. 1 and generally designated by reference letter A, comprises a massage head (1) designed to be removable from the drive housing (2). The massage head (1) is designed to exert a mechanical action on a user's facial skin by means of massage components (E) driven by an electric motor.

To this end, the drive housing (2) comprises an elongated body (3) that is generally cylindrical in shape, which comprises, at one of its ends (4) an adaptation means (5) that is removable from the massage head (1). The adaptation means (5) is, in the example illustrated, formed by a sheath, into which the massage head (1) is partially inserted.

The drive housing (2) comprises, inside the body (3), an electric motor (6) that actuates a drive means (7) designed to transmit the movement of the electric motor to the massage components of the massage head (1). In the example illustrated, the drive means (7) comprises a reducer, not depicted, which drives an output shaft (8) accessible at the adaptation means (5) of the drive housing (2).

The electric motor (6) is operated by a control unit (10) powered by a battery pack (B) positioned inside the body (3). Of course, the electric power for the control unit (10) could also come directly from the power grid by means of a transformer. The control unit (10) is also connected to a manual control interface (11) accessible from the exterior of the body (3). The manual control interface (11) may, for example, include a start/stop switch and/or a means of manually selecting the operating programs.

The drive housing (2) also comprises a means of recognition (12) that is attached to the control unit (10) and that is designed to read the identification means (13) carried by the massage head (1). The control unit (10) is then designed to control the operation of the massage device (A) depending on the massage head (1) as recognized upon reading the identification means (13). Control of the operation of the massage device (A) may, in particular, consist of determining the spin speed of the electric motor (6), such that it is appropriate for the massage performed by the massage components (E). The identification means (13) may, for example, consist of an RFID chip, while the recognition means (12) will be designed to read such an RFID chip. Of course, the identification means (13) and recognition means (12) may be made in any other appropriate manner, such as in the form of an identification system by mechanical or electrical contact, for example, or even in the form of a magnetic identification system using permanent magnets and reed switches.

In the invention, the massage head (1) is designed to perform a pinching massage. To this end, the massage head (1) comprises, as massage components (E), two massage rollers (21 and 22) that are mobile in rotation on themselves about two rotational axes ($\Delta$ and $\Delta'$) parallel to each other and to an application surface (S) that is more visible in FIG. 2. The two massage rollers (21 and 22) are set apart from each other by a working area (Z). In the example illustrated, the distance between the rotational axes ($\Delta$ and $\Delta'$) is constant.

Moreover, in the example illustrated, the massage rollers (21 and 22) are arranged inside the massage head (1) such that a plane (P) tangent to the two rollers and situated toward the outside the massage head, forms a non-zero, non-right angle with a longitudinal axis of the drive housing (2).

As described in the invention, a first roller (21) comprises at least one paddle, and in the case depicted as an example, four paddles (23 through 27), which protrude radially from the surface of the first roller (21). The peripheral surface of the first roller (21) is set back from the application surface (S). The paddles (23 through 27) extend radially enough to protrude from the application surface (S) as the first roller (21) spins. The paddles (23 through 27) are also distributed regularly around the periphery of the first roller (21) and are, in this case, placed at 90° from one another.

Figure 7:
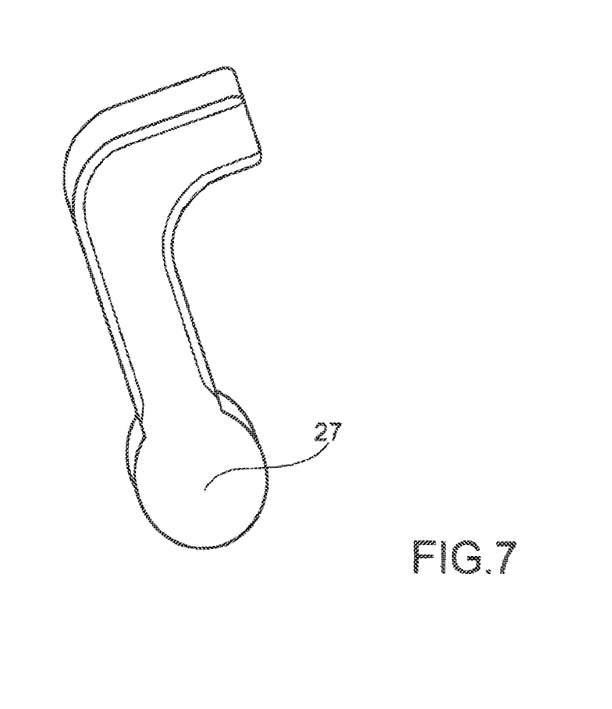
FIG. 7 is a perspective view of an alternative method to FIGS. 1 through 5 of a paddle of the roller described in the invention.

In the example illustrated, the paddles (23 through 27) have straight crosswise cross-sections, which can be seen in different shapes in FIGS. 1 and 7, with the understanding that all of the paddles may have the same shape. Thus, Paddle 23 has, viewed in its straight crosswise cross-section, one free end that is thicker than the rest of the paddle (23). As for Paddle 24, viewed in its crosswise straight cross-section, is shaped like a figure-8. Paddle 25 viewed in its crosswise straight cross-section is straight in shape. Lastly, Paddle 26 has a crosswise straight cross-section that is elongated and slender in shape, the thickness of which tapers toward the end. In other words, this shape may take the form widely known as a comma, the concavity of which, for example, at rest, is oriented opposite the spinning direction of the first roller (21) as will become apparent below. Another paddle shape (27) is illustrated in FIG. 7, in which the crosswise straight cross-section is in the shape of an uppercase L, the base of which is at the free end of the paddle. Each of these shapes produces a massage of differing intensity and effect.

The second roller (22) has a smooth-type peripheral surface that protrudes from the application surface (S) or extends to the side of the application surface (S).

We defined the smooth-type surface above. As illustrated in FIGS. 1 through 5, the smooth-type surface of the roller (22) may be absolutely smooth. FIG. 6 illustrates an alternative mode of the smooth-type surface: the surface is fluted parallel to the height of the roller, in a regular manner. Thus, when the roller is in contact with the skin, it defines an angle of pressure (Sa), of which it can be assumed that at least approximately half of the outside surface contained within the angle (Sa) of pressure of the roller toward the skin is in contact with the skin.

In the invention, the massage head (1) also comprises a means of transmission (30) designed to spin the rollers (21 and 22) simultaneously in the same direction, moving from outside the working area to inside the working area for the first roller, and from inside to outside the working area for the second roller, when viewed from outside the massage head and as indicated by Arrows F1 and F2. The transmission means (30) are then designed to cooperate with the drive means (7) and more particularly with the output shaft (8) so as to transmit and transform the spinning movement of the electric motor about Longitudinal Axis L into spinning movements about Axes Δ and Δ' which have an orthogonal direction to that of Longitudinal Axis L.

Figure 3:
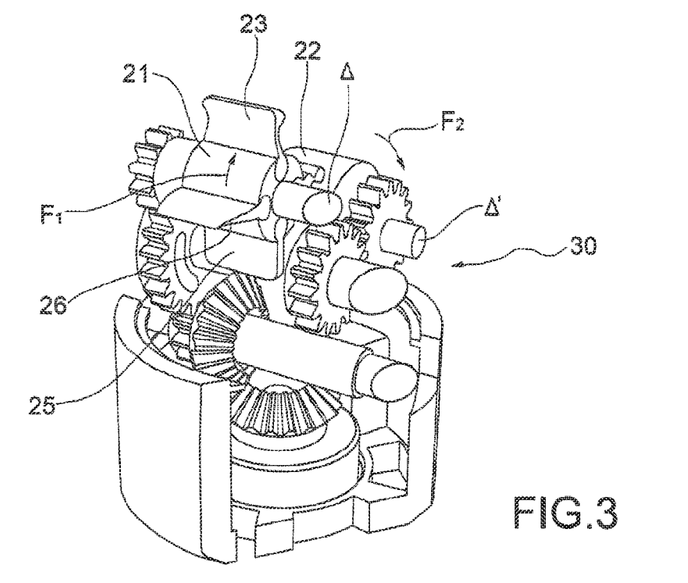
FIG. 3 is a fragmented, perspective view of the massage head illustrated in FIG. 2.

In the example illustrated and as depicted in FIG. 3, the transmission means (30) comprises a gear box comprising, firstly, two gearwheels shaped like truncated cones ensuring an angle transmission and, secondly, straight gearwheels that drive the massage rollers (21 and 22) together, at a different speed.

The transmission means (30) are preferably designed to spin the first roller (21) at a faster speed than the second roller (22), and in this case double that of the second roller (22).

The massage device thus created is implemented as follows. The application surface (S) is placed against the face, the user then turns on the massage device (A) using the interface (11), and the massage rollers (21 and 22) begin to spin in the same direction. The spinning of the second roller (22) causes the massage head to move over the skin, while the paddles of the first roller (21) reproduce the pinching effect on the skin, as the spacing between the paddles makes it possible to release the skin successively, as the massage head moves forward.

Figure 2:
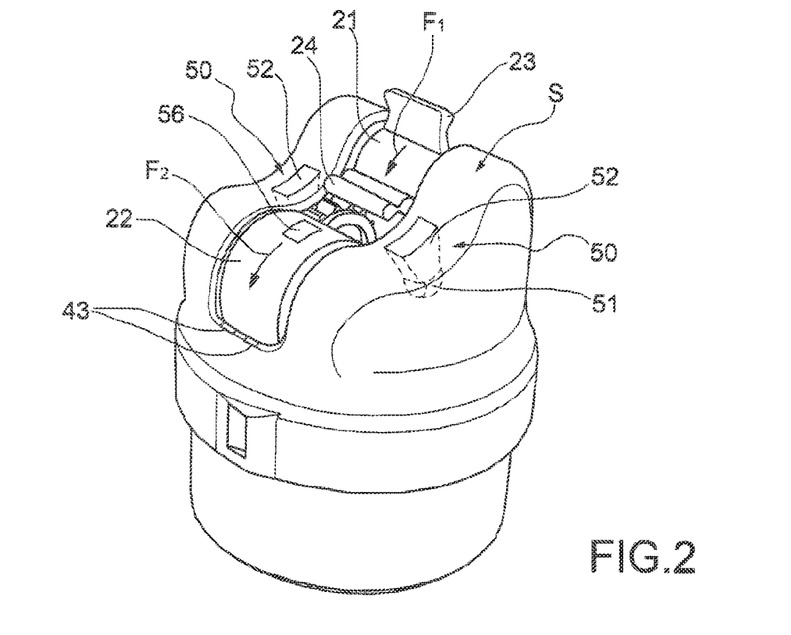
FIG. 2 is a partially perspective view of the removable massage head equipping the massage device illustrated in FIG. 1.

The massage performed by the device described in the invention makes it possible, in particular, to reduce wrinkles by stimulating blood circulation in the facial skin or even in the skin of the neck. In order to optimize this treatment, the massage device (A) as illustrated in FIGS. 1 through 3, comprises a means (40) of applying a cosmetic product. In the example illustrated, the means of applying a cosmetic product (40) comprises a reservoir (41) situated in the drive housing (2) and connected, via a withdrawing pump (42), to two dispensing nozzles (43) situated in the application surface (S) and more specifically in the immediate proximity of the second massage roller (22) as shown in FIG. 2. Thus, the cosmetic product is applied to the skin by the second massage roller. The withdrawing pump (42) is operated by the control unit (10) so as to dispense the cosmetic product while the massage device (A) is operating.

Of course, the application surface (S) may include only a single dispensing nozzle or even multiple dispensing nozzles arranged differently. Likewise, the one or more cosmetic product dispensing nozzles could be arranged inside the massage head (1) so as to apply the cosmetic product over either one, or even both of the massage rollers.

Moreover, still in reference to the example illustrated in FIGS. 1 through 3, the massage device (A) also comprises a means of applying an electric current (45) that comprises a unit (46) that generates an electric current and/or voltage. The generator unit (46) is operated by the control unit (10). The generator unit (46) is connected by a brush system (47) to an electrode (56) formed at least partially by the conductive surface of the second roller (22).

While the massage device (A) is in use, the control unit (10) directs the operation of the generator unit (46) such that, for example, a micro-current is applied to stimulate the facial skin or muscles, or an electrophoresis phenomenon is produced to promote the absorption of the cosmetic product's active ingredients.

In the example illustrated in FIGS. 1 through 3, the massage head (1) comprises a means (50) of diffusing light toward the face. In this case, the diffusion means (50) is arranged in the massage head, and more specifically, on the application surface (S). The diffusion means (50) comprises, as a light source, two electroluminescent diodes (51) operated by the control unit (10) and arranged on either side of the working area (Z). These light sources (51) are then each combined with an optical system (52) formed by transparent blocking that forms a light guide and that comprises a light output surface situated at the level of the pressure surface (S) and is therefore designed to be oriented toward the face of the user of the massage device (A) described in the invention.

Figure 4:
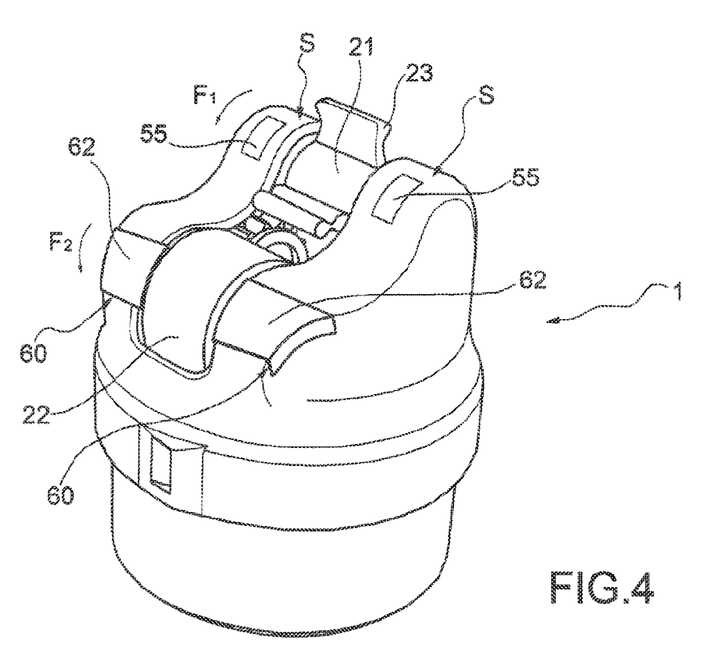
FIG. 4 is a perspective view of another method of implementing a removable massage head for a massage device described in the invention.
Figure 5:
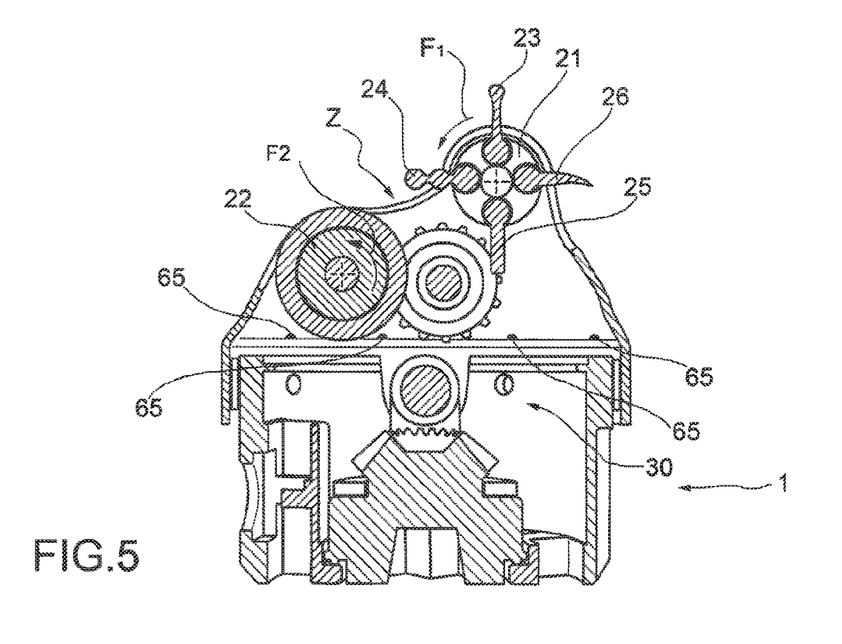
FIG. 5 is a cross-section illustration of the massage head illustrated in FIG. 4.
Figure 6:
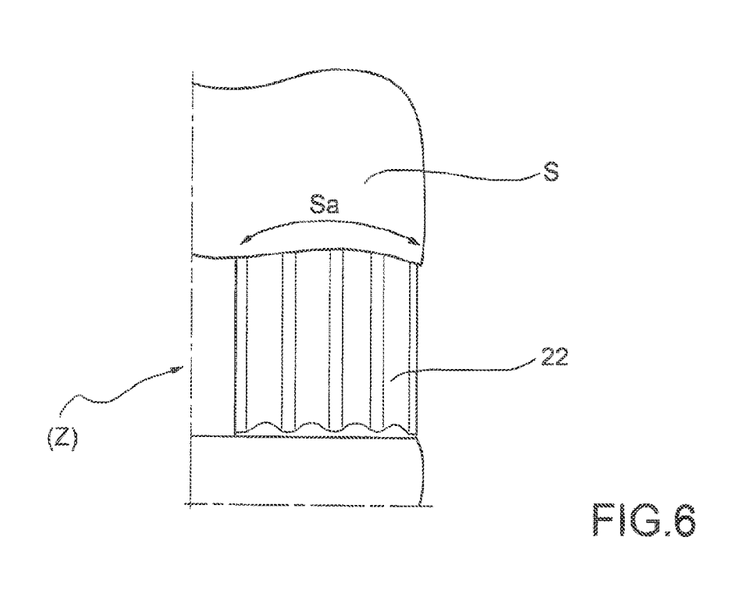
FIG. 6 is a perspective view of an alternative method to FIGS. 1 through 5 of implementing a roller with a smooth-type surface as described in the illustrated invention.

FIGS. 4 and 5 depict one variation for implementing a massage head for a massage device described in the invention, which differs from the one described in reference to FIGS. 1 through 3, in that the application surface (S) comprises two electrodes (55) connected to the electric current generator unit (46).

In this same example of implementation, the massage head (1) also comprises, as a means of dispensing the cosmetic product, two caps (60) designed to be removable from said massage head (1). Each cap (60) then comprises a swab (62) soaked with the cosmetic product.

Moreover, in this variation, the diffusion means (50) is arranged in the massage head and comprises, as a light source, electroluminescent diodes (65) operated by the control unit (10). The electroluminescent diodes (65) light up the inside of the massage head (1), such that the massage area forms a light output surface. In this respect, the upper part of the massage head could also be transparent, such that the application surface (S) would form a light output surface.

It is also possible for the device described above not to comprise a motor. In this case, the device is only used manually and comprises:

A massage head comprising:
  Two parallel massage rollers that are mobile in rotation on themselves about two rotational axes that are parallel to each other and to the application surface, set apart from each other, being separated by a working area, a first roller comprising at least one paddle that protrudes radially from the surface of the first roller, and the second roller having a smooth-type surface,
  And a drive housing that carries the massage head
A plane tangent to the two rollers and situated toward the outside of the massage head, forms a non-zero, non-right angle with a longitudinal axis of the housing.

All other characteristics are identical to the motorized device described above.

Of course, various other modifications or variations of the device and the massage head described in the invention may be considered within the scope of the attached claims.

The invention claimed is:

1. A facial massage device comprising:
  a massage head that comprises:
  two parallel massage rollers that are mobile in rotation on themselves about two rotational axes parallel to each other and parallel to an application surface, set apart from each other, being separated by a working area, a first roller comprising at least one paddle that protrudes radially from a surface of the first roller, and a second roller having a smooth surface,
  a transmission means designed to spin the rollers in a same direction, the first roller moving from outside the working area to inside the working area, and the second roller moving from inside the working area to outside the working area, when viewed from outside the massage head, and
  a drive housing that carries the massage head and that comprises an electric motor that actuates drive means designed to transmit movement of the electric motor to a transmission means,
  wherein the drive housing is substantially cylindrical with a longitudinal axis extending along a length of the drive housing and between the two parallel massage rollers, and
  wherein a plane tangent to the two rollers and situated toward an outside of the massage head forms a non-zero, non-right angle with the longitudinal axis of the drive housing, wherein the massage head is removable from the drive housing, wherein the massage head further comprises an identification means, and wherein the drive housing comprises a means of recognizing the identification means connected to a control unit designed to control the operation of the massage device depending on the massage head recognized.

2. The massage device described in claim 1, wherein the transmission means comprises a gear box designed to spin the rollers simultaneously.

3. The massage device described in claim 1, wherein the transmission means comprises a gear box designed to ensure that a spinning speed of the first roller is greater than the spinning speed of the second roller.

4. The massage device described in claim 3, wherein the transmission means comprises a gear box designed to ensure that the spinning speed of the first roller is between double and triple the spinning speed of the second roller.

5. The massage device described in claim 1, wherein the at least one paddle is at least two paddles distributed evenly around a periphery of the first roller.

6. The massage device described in claim 1, wherein the first roller comprises at least one paddle that, in its crosswise straight cross-section, is straight in shape.

7. The massage device described in claim 1, wherein the first roller comprises the at least one paddle that, in its crosswise straight cross-section, has a figure eight shape.

8. The massage device described in claim 1, wherein the first roller comprises the at least one paddle that, in its crosswise straight cross-section, is elongated and slender in shape, a thickness of which tapers toward an end.

9. The massage device described in claim 1, wherein the first roller comprises the at least one paddle that, in its crosswise straight cross-section, has one free end that is thicker than the rest of the at least one paddle.

10. The massage device described in claim 1, wherein the first roller comprises the at least one paddle that, in its crosswise straight cross-section, is in the shape of an upper-case L, a base of which is at a free end of the at least one paddle.

11. The massage device described in claim 1, further comprising a means of applying an electric current comprising at least one electrode that is designed to be in contact with a user's skin and that is connected to one of an electric current or voltage generator unit.

12. The massage device described in claim 11, wherein the massage head comprises an application surface (S) designed to come at least partially into contact with the user's skin.

13. The massage device described in claim 12, wherein the application surface (S) carries the at least one electrode.

14. The massage device described in claim 13, wherein at least one of the two rollers carries or forms the at least one electrode.

15. The massage device described in claim 1, further comprising a light diffusing means.

16. The massage device described in claim 15, wherein the light diffusion means comprises at least one light source and at least one optical diffusion system comprising an output surface designed to be oriented toward a user's face.

17. The massage device described in claim 16, wherein the application surface (S) comprises a light output surface.

18. The massage device described in claim 16, wherein the massage head comprises a light output surface situated facing the working area (Z).

19. The massage device described in claim 16, further comprising a means of applying a cosmetic product.

20. The massage device described in claim 19, wherein the cosmetic product application means comprises at least one cap comprising a swab that is adapted to be soaked with the cosmetic product and which is designed to be removable from the massage head.

21. The massage device described in claim 20, wherein the cosmetic product application means comprises a reservoir of the cosmetic product and at least one dispensing nozzle connected to a system of withdrawing the cosmetic product from the reservoir.

22. The massage device described in claim 21, wherein the cosmetic product application means comprises at least one dispensing nozzle situated in one of the massage head or on the application surface (S).

23. The massage device described in claim 1, wherein the massage head is removable from the drive housing.

24. A facial massage device comprising:
a massage head that comprises:
two parallel massage rollers that are mobile in rotation on themselves about two rotational axes parallel to each other and parallel to an application surface, set apart from each other, being separated by a working area, a first roller comprising at least one paddle that protrudes radially from a surface of the first roller, and the second roller having a smooth surface, and
a drive housing that carries the massage head, and comprises an electric motor,
wherein the drive housing is substantially cylindrical with a longitudinal axis extending along a length of the drive housing and between the two parallel massage rollers, and
wherein a plane tangent to the two rollers and situated toward an outside of the massage head forms a non-zero, non-right angle with the longitudinal axis of the drive housing, wherein the massage head is removable from the drive housing, wherein the massage head further comprises an identification means, and wherein the drive housing comprises a means of recognizing the identification means connected to a control unit designed to control the operation of the massage device depending on the massage head recognized.

25. The massage device described in claim 24, wherein the massage head comprises a transmission means designed to spin the rollers in a same direction, the first roller moving from outside the working area (Z) to inside the working area (Z), and the second roller moving from inside the working area to outside the working area, when viewed from outside the massage head.

26. The massage device described in claim 24, wherein the drive housing comprises an electric motor actuating a drive means to transmit movement of the electric motor to a transmission means.

27. The massage device described in claim 26, wherein the transmission means comprises a gear box designed to spin the rollers simultaneously.

28. The massage device described in claim 27, wherein the gear box is designed to ensure that the spinning speed of the first roller is greater than the spinning speed of the second roller.

29. The massage device described in claim 28, wherein the spinning speed of the first roller is between double and triple the spinning speed of the second roller.

30. The massage device described in claim 24, wherein the at least one paddle is at least two paddles distributed evenly around a periphery of the first roller.

31. The massage device described in claim 24, wherein the at least one paddle that, in its crosswise straight cross-section, is straight in shape.

32. The massage device described in claim 24, wherein the first roller comprises the at least one paddle that, in its crosswise straight cross-section, has a figure eight shape.

33. The massage device described in claim 24, wherein the first roller comprises the at least one paddle that, in its crosswise straight cross-section, is elongated and slender in shape, a thickness of which tapers toward an end.

34. The massage device described in claim 24, wherein the first roller comprises the at least one paddle that, in its crosswise straight cross-section, has one free end that is thicker than the rest of the at least one paddle.

35. The massage device described in claim 24, wherein the first roller comprises the at least one paddle that, in its crosswise straight cross-section, is shaped like an uppercase L, a base of which is at a free end of the at least one paddle.

36. The massage device described in claim 24, further comprising a light diffusing means.

37. The massage device described in claim 36, wherein the light diffusing means comprises at least one light source and at least one optical diffusion system comprising an output surface designed to be oriented toward a user's face.

38. The massage device described in claim 37, wherein the application surface (S) comprises a light output surface.

39. The massage device described in claim 37, wherein the massage head comprises a light output surface situated facing the working area.

40. The massage device described in claim 24, further comprising a means of applying a cosmetic product.

41. The massage device described in claim 40, wherein the means of applying the cosmetic product comprises at least one cap comprising a swab that is adapted to be soaked with the cosmetic product and is removable from the massage head.

42. The massage device described in claim 40, wherein the means of applying the cosmetic product comprises a cosmetic product reservoir and at least one dispensing nozzle connected to a system for withdrawing the cosmetic product from the reservoir.

43. The massage device described in claim 42, wherein the means of applying the cosmetic product comprises at least one dispensing nozzle situated in one of the massage head or the application surface (S).

44. A facial massage device comprising:
a massage head that comprises:
two parallel massage rollers that are mobile in rotation on themselves about two rotational axes parallel to each other and parallel to an application surface, set apart from each other, being separated by a working area, a first roller comprising at least one paddle that protrudes radially from a surface of the first roller, and a second roller having a smooth surface,
a transmission means designed to spin the rollers in a same direction, the first roller moving from outside the working area to inside the working area, and the second roller moving from inside the working area to outside the working area, when viewed from outside the massage head, and
a drive housing that carries the massage head and that comprises an electric motor that actuates drive means designed to transmit movement of the electric motor to a transmission means,
wherein the massage head is removable from the drive housing,
wherein the massage head further comprises an identification means, and
wherein the drive housing comprises a means of recognizing the identification means connected to a control unit designed to control the operation of the massage device depending on the massage head recognized.

\* \* \* \* \*